United States Patent [19]

Motoyama et al.

[11] Patent Number: 4,769,945

[45] Date of Patent: Sep. 13, 1988

[54] DELIVERY UNIT OF PLANT TISSUE

[75] Inventors: Shimesu Motoyama, Asaka; Seiichi Umeda, Tsurugashima; Hiroaki Ogishima, Tokorozawa; Sashiro Motegi, Ageo, all of Japan

[73] Assignee: Kirin Brewery Co., Ltd., Tokyo, Japan

[21] Appl. No.: 8,737

[22] Filed: Jan. 30, 1987

[30] Foreign Application Priority Data

Jan. 31, 1986 [JP] Japan .................................. 61-18066

[51] Int. Cl.$^4$ .............................................. A01C 1/06
[52] U.S. Cl. ......................................... 47/57.6; 47/58; 47/74
[58] Field of Search ....................... 47/57.6, 74, 77, 58

[56] References Cited

U.S. PATENT DOCUMENTS

| 1,446,113 | 2/1923 | Blackwell | 47/74 |
| 4,628,633 | 12/1986 | Nilsson | 47/57.6 |

FOREIGN PATENT DOCUMENTS 6299  1/1980  European Pat. Off. ............... 47/74

*Primary Examiner*—Robert E. Bagwill
*Attorney, Agent, or Firm*—Kane, Dalsimer, Sullivan, Kurucz, Levy, Eisele and Richard

[57] ABSTRACT

A delivery unit of plant tissue of the present invention comprises a vessel in which meristematic tissue having the ability to grow into an entire plant body through differentiation is received. The body of the vessel is made of water-soluble substance and the interior thereof is covered with a water-insoluble substance. Hydrogel is charged in the vessel and the meristematic tissue is held by the hydrogel in a state in which its root or rooting portion is embedded therein or it is placed on the hydrogel. The vessel has a structure of a closed type with a cap or an open type. When the delivery unit of plant tissue is seeded in a medium, the water-soluble substance of the vessel body is dissolved by water contained in the medium and the bud and root grown out of the meristematic tissue breaks the thin film made of a water-insoluble substance which is provided in the interior of the vessel so as to further grow out.

19 Claims, 2 Drawing Sheets

DELIVERY UNIT OF PLANT TISSUE

BACKGROUND OF THE INVENTION (1) Field of the Invention

The present invention relates to the compositions containing plant meristematic tissues.

(2) Related Art Statement

The breeding of plants has been conventionally achieved by fixing a superior characteristic acquired by crossing or the induction of mutation as a specific variety (fixed variety). In addition, techniques such as gene recombination and cell fusion have recently led to an employment.

However, anyone of the techniques requires, for particularly an annual plant, the process in which seeds are gathered from parent plants possessing a superior characteristic and these are sown in order to obtain offspring having the same characteristics as these parent plants. Such a breeding method with seeds requires much labor and time and a particular technique for producing a fixed variety and always involves the danger that the characteristics of the fixed variety once produced will deteriorate as a result of natural crossing.

When a useful variety is established as an $F_1$ hybrid or obtained by a specific chromosomal pattern such as aneuploidy, heterozygosis of structural mutation, or triploidy, it is substantially impossible to cause certain characteristics to be inherited in the coming generation by seed propagation. In these circumstances, it is necessary to gather new seeds by crossing parent plants for each generation, or to obtain seeds by means of a particular treatment. These methods are complicated and, in some cases, involve the possibility of creating an extremely undesirable situation in that it is necessary to depend upon the supply of useful seeds from a particular institution.

Furthermore, propagation methods with seeds require much labor and time and involve disadvantage in being restricted by the weather and the type of land employed.

A technique of vegetative propagation has been developed for the purpose of overcoming the above-mentioned disadvantages, in which meristematic tissues such as somatic embryo, adventitious bud, shoot primordium, or callus which are obtained by culturing parts of the tissue of a plant body are further cultured to encourage shooting and obtain a plant body. Although in some cases this method causes a change in the number of chromosomes, by selecting the conditions, it is possible to obtain a clone having completely the same character as that of the original plant, whereby it is possible in principle to breed from one parent plant large numbers of offspring for several generations without limit.

However, natural seeds possess an embryo which later grows into an entire plant body, and botanical accessories such as an endosperm which becomes nutrient for the embryo and a seed coat for physically protecting the embryo. The botanical accessory serves to prevent the embryo from withering and germinating while in a state of preservation and to control the water content at a suitable level for the purpose of preventing decomposition. In contrast, meristematic tissues obtained by culturing tissue possess no botanical accessory of the type described above and are thus presented in a completely defenseless and exposed state.

The analogue of seed containing such uncovered meristematic tissues are disclosed in Japanese Patent Laid-Open Nos. 59(1984)-102308 and 60(1985)-118103. A subject matter thereof comprises the formation of the analogue of seed by encapsulating meristematic tissues in a gel matrix for the purpose of giving nutrients thereto.

However, such gel-encapsulation involves disadvantage in that the gel is difficult to handle and inferior in shelf life because of its low strength and the fact that it contains a large amount of water. In order to overcome this problem, a method of hardening the gel surface by a treatment with an agent such as glutaraldehyde is disclosed in the above-described Laid-Open Publications, but these offer an insatisfactory effect and are far from solving the problem.

In addition, faults are experienced since meristematic tissues are completely encapsulated in gel, so the tissues are insufficiently supplied with oxygen during germination and formation of root and are often hindered from growing and withered, and since the gel has large strength, so the gel is not broken and plumules are sometimes captured in the gel, depending upon the growing power of the meristematic tissues.

SUMMARY OF THE INVENTION

It is an object of the present invention to provide a technique which is capable of facilitating the handling of meristematic tissues with respect to their delivery until said meristematic tissues are planted and of supplying sufficient oxygen to meristermatic tissues so as to improve the germination and formation of root thereof.

It is another object of the present invention to provide a technique which is capable of preventing the hindering of plumule's growth even when a gel has large strength.

A delivery unit of plant tissue of the present invention comprises a hydrogel-charged vessel the inner surface of which is covered with a water-insoluble substance and meristematic tissue received therein.

In the present invention, the above-described configuration of a delivery unit enables the vessel which forms the skeleton of the delivery unit to have the function of allowing the hydrogel to be stably received therein, its body being easily dissolved by water contained in a field after seeding, and its covering substance being easily broken during the germination and growth of root.

In addition, the meristematic tissues are brought into contact with the hydrogel so that it becomes possible to supply water from the hydrogel to the meristematic tissues and the meristematic tissues are at least partly exposed, whereby it is possible to supply sufficient oxygen to the meristematic tissues. The above-described objects can be achieved in a combination of the above functions.

The other objects and characteristics of the present invention will become clear from the following description.

The above-described delivery unit will now be described in detail.

The vessel used in the present invention comprises a body made of a water-soluble substance having sufficient mechanical strength to maintain the form and to maintain and support the contents, the inner side thereof being thinly covered with a water-insoluble substance which is insoluble in water and permits substantially no water to permeate therethrough. That is to say, the delivery unit is required to have an enough mechanical strength in the steps of storing, transporting, and seeding, but it need not have strength after seeding. It is rather necessary to prevent the hindering of growth of germinated or rooted plants. In the present invention, therefore, the vessel body can be softened and dissolved by water in soil and the inner surface of the vessel body is covered with a substance which is insoluble in water and permits substantially no water to permeate therethrough so that it is not dissolved and swollen by water from the hydrogel, which is a medium.

Water-soluble substances used for forming the vessel body may include any substances which can achieve the above objects and are harmless to plants. Examples of such substances are water-soluble polymers such as gelatin, casein, starch, pullulan, sodium alginate, methyl cellulose, hydroxyethyl cellulose, hydroxypropyl cellulose, hydroxypropylmethyl cellulose, polyvinyl alcohol, sodium polyacrylate, polyacrylamide, polyoxyethylene, and polyvinyl pyrrolidone, but the water-soluble substances are not limited to these substances. A plasticizer which is suitable for such water-soluble substances may be added to them if necessary. The water-insoluble substance used as covering on the interior may include any substances which do not permit water from the hydrogel received in the vessel to permeate therethrough and which are harmless to plants. Examples of such substances are (1) synthetic resins, i.e., vinyl resins such as polyethylene, polypropylene, polystyrene, polymethyl methacrylate, polyvinyl chloride, polyvinyl acetate, and ethylene-vinyl acetate copolymer; modified vinyl resins such as polyvinyl formal and polyvinyl butyral; or poly polycondensation resins such as polyamides, polyesters, and polyethers; (2) natural resins such as shellac, gutta percha, copal, and dammar; (3) synthetic or natural rubbers such as polychloroprene, polyisoprene, polyurethane, butyl rubber, EPT, NBR, SBR, and silicone rubber; (4) cellulose derivatives such as ethyl cellulose, cellulose acetate, cellulose propionate, and nitrocellulose; or (5) fats, oils, or wax. However, the water-insoluble substances are not limited to these substances. As a matter of course, covering with the water-insoluble substances may be perfomed by painting, spraying, or any other methods.

Desirable types of hydrogel received in the vessel may include substances which do not hinder meristematic tissues from germinating and forming root but which promote the germination and formation of root. A known agar medium is generally preferable, but any substances which can achieve this object may be used, for example, sodium alginate, pectine, mannan, carrageenan, and gellan gum (trade name Gelrite, produced by Kelco Division of Merk Co., Ltd.) which is a polysaccharide produced by bacteria may be used. However, the hydrogel is not limited to these substances. The hydrogel mainly comprises such a polymeric substance and water and is in a gel state. There will be no difficulty if the hydrogel contains one or more substances selected from at least one of the groups of nutrients, plant growth hormones, fungicides, bactericides, water-retaining agents, and pH adjusting agents. It is particularly preferable to add nutrients and when the vessel of the delivery unit is of an open type, it is preferable to add fungicide and/or bactericide.

Meristematic tissues which are the object of the present invention are tissues which are capable of directly growing into entire plant bodies or after they have passed through differentiation and organogenesis, and which exclude seed. In particular, somatic tissue, zygotic tissue, or germ line tissue may be used, and more particularly, somatic tissue may include meristematic tissue expressed as definite bud, adventitious bud, somatic embryo, shoot primordium, protocorm-like body, or green spot. The kinds of plant which can be employed include all plants which can provide such meristematic tissues without any particular restriction. As plant forms having great practicability, major crops such as rice, wheat, barley, corn, and soybean; vegetables such as celery, parsley, lettuce, cauliflower, carrot, eggplant, tomato, onion, garlic, ginger, strawberry, watermelon, and asparagus; industrial crops such as rape, sugar cane, sugar beet, and tobacco; medical plants such as belladonna, ginseng, fennel; and ornamental plants such as chrysanthemum, gladiolus, lily, orchid, amaryllis, geranium, begonia, African violet, fern, and poinsettia, may be exemplified.

In the present invention, it is necessary that the meristematic tissues are brought into contact with the hydrogel and at least partly exposed to the air. In other words, at least part of the meristematic tissues is brought into contact with the hydrogel so as to absorb water or nutrients in it. Furthermore, if necessary, part of the meristematic tissues may be fixed by embedding them in the above-described hydrogel so that the meristematic tissues are prevented from scattering or being lost. In addition, it is necessary that at least part of the meristematic tissues is exposed to the air for the purpose of preventing the hindering of germination and facilitating the supply of oxygen from the air.

Examples of the delivery unit of plant tissue in accordance with the present invention will now be described with reference to drawings of representative structures thereof. As a matter of course, various types of structure may be employed in accordance with specific objects.

DESCRIPTION OF THE PREFERRED EMBODIMENTS

In the various embodiments of the delivery unit of plant tissue of the present invention shown in FIGS. 1 to 7, FIGS. 1 to 3 respectively show delivery units of a closed type and FIGS. 4 to 7 respectively show delivery units of an open type.

Figure 1:
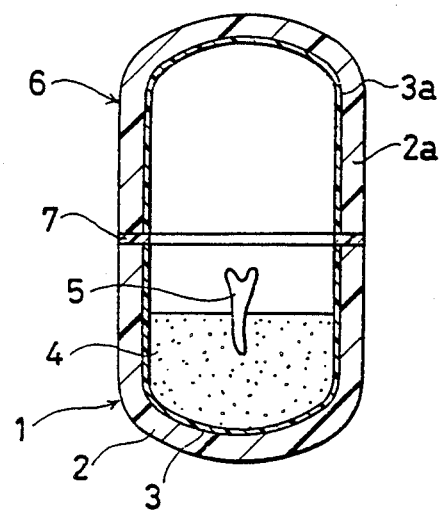
FIG. 1 is a sectional view of an embodiment of the delivery unit of plant tissue in accordance with the present invention.

In the delivery unit shown in FIG. 1, a vessel 1 comprises a vessel body 2 formed of a water-soluble substance and a thin film 3 which coveres the interior thereof and made of a water-insoluble substance. Hydrogel 4 is charged in the vessel 1 and a meristematic tissue 5 is fixed to the hydrogel 4 in a partly-inserted state. A cap 6 comprising a cap body 2a having the same structure as that of the vessel 1 and a thin film 3a is mounted on the open end of the vessel 1 by an adhesive 7, so that the meristematic tissue 5 is sealed in the vessel 1.

In the delivery unit shown in FIG. 1, after seeding, the vessel body 2 and the cap body 2a are dissolved to in the surrounding water, such as water in the soil and rainwater, to disappear thereby, while the thin films 3 and 3a remain, though the thin film 3 will be easily destroyed by the growth of a bud or root.

Figure 2:
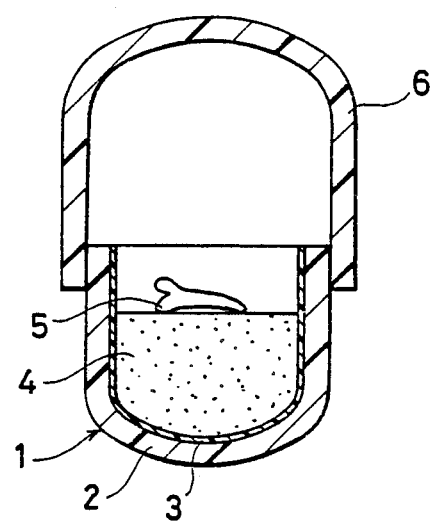
FIGS. 2 to 7 are sectional views of various other embodiments of the delivery unit of plant tissue in accordance with the present invention.

The delivery unit shown in FIG. 2 is fundamentally similar to that shown in FIG. 1. The differences are that the meristematic tissue 5 is provided on the surface of hydrogel 4 and brought into contact with it and the cap 6 is made only of a water-soluble substance. In this delivery unit of plant tissue, after seeding, the cap 6 is dissolved in water to disappear, so that it is easily changed into an open type.

Figure 3:
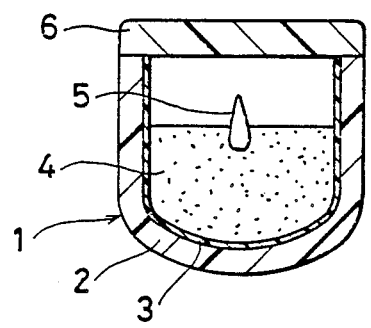

The delivery unit shown in FIG. 3 is similar to that shown in FIG. 2 and different from the latter with respect to the meristematic tissue 5 inserted into hydrogel 4 and the cap 6 which has a substantially flat form.

It is a matter of course with each of the delivery unit shown in FIGS. 1 to 3 that the vessel 1 may be made of a material which is the same as that of the cap 6, or materials which are different in physical properties may be used in combination.

In the delivery units of the closed type, the meristematic tissues need not always be fixed to the hydrogel and may be brought into contact with the hydrogel during seeding.

Figure 4:
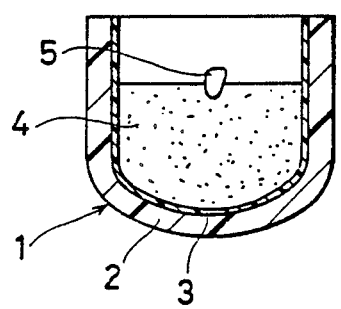

In the delivery unit shown in FIG. 4, a vessel 1 is fundamentally the same as those shown in FIGS. 1 to 3 but the upper end thereof is initially open because there is no cap.

Figure 5:
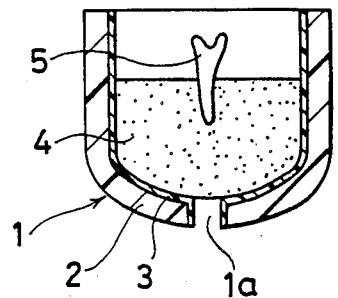

In the delivery unit shown in FIG. 5, a hole 1a is provided on the bottom of a vessel 1, the other elements being similar to those shown in FIG. 4. In this delivery unit, the hole 1a enables the absorption of water from the soil and prevents the hindering of the growth of a root.

Figure 6:
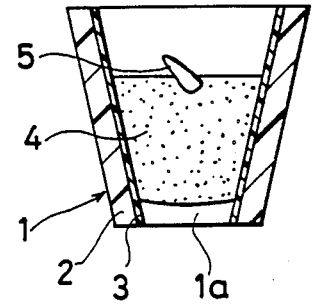

The delivery unit shown in FIG. 6 corresponds to that provided with a hole 1a which is larger than the hole shown in FIG. 5 and the side of the vessel 1 is substantially linear and has a certain degree of taper, the hydrogel 4 being held by the taper.

Figure 7:
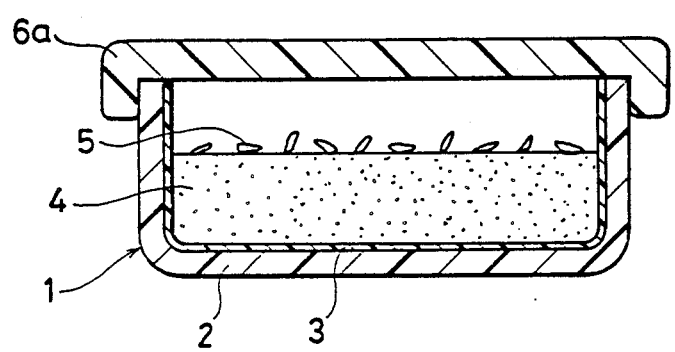

The delivery unit shown in FIG. 7 has a fundamental structure which is common to that shown in FIG. 4 but is different with respect to a large vessel 1 in which a plurality of meristematic tissues are received and which is sealded by a cap 6a made of a water-insoluble substance. The cap 6a is removed when the unit is seeded so that it is used in the open state. The delivery units of the present invention enable the direct planting of meristematic tissues in a nursery or field, without employing any particular facilties, which usually cannot be planted unless they are cultured and then conditioned.

Particularly, in the case of the closed type, it is possible to maintain the interior in a sterile condition for a given time and to so design that the sterile condition is broken after plant bodies are germinated or grown. In the case of the open type, it is preferable to prevent a contamination from the outside by adding fungicide and/or bactericide.

The present invention will now be described in detail with reference to examples.

[EXAMPLE 1]

Example 1 of the present invention concerns an example of the delivery unit which is shown in FIG. 1.

The interior of a vessel body 2 comprising a body of the Japanese pharmacopoeia No. 1 capsule which was formed of gelatin (a water-soluble substance) containing glycerin as a plasticizer, was painted with an 8% (w/w) ethyl acetate solution of nitrocellulose, using a thin writing brush, and subjected to air drying. Consequently, a vessel 1 whose interior was covered with a thin film 3 of nitrocellulose (a water-insoluble substance) having a thickness of about 10 $\mu$m was formed. About 0.2 g of an agar medium of Murashige-Skoog (referred to as "MS" hereinafter) was charged into this vessel, and a somatic embryo of carrot (*Daucus carota* L.) was inserted into the vessel 1 in a state in which the shoot axis thereof was exposed to the air and the root axis thereof was inserted into the medium. Then a cap 6 formed by covering the interior of the body of the Japanese pharmacopoeia No. 1 capsule in the same manner as described above, and which had the same structure as that of the above-described vessel, was prepared, and the 8% (w/w) ethyl acetate solution of nitrocellulose was applied to the surface at the open end thereof. The open end was then combined with the end of the vessel 1 in which the adventitious embryo was inserted so as to be bonded thereto. As a result, a delivery unit having the structure shown in FIG. 1 was obtained. All the operations were conducted under sterile conditions.

When the delivery unit obtained in this manner had been seeded, the somatic embryo in the delivery unit rooted after 5 days in an incubator at 25° C., the hypocotyl grew after 7 days, and germination took place after 10 days. Otherwise, the delivery unit was planted in the soil in a field until the top thereof was substantially buried, whereupon the vessel body 2 and the cap body 2a which formed the outer layer thereof were gradually dissolved by water contained in the soil until only the thin films 3 and 3a of nitrocellulose in the interior remained after 10 days. These thin films 3 and 3a were destroyed as the carrot grew, and the carrot grew out well.

[EXAMPLE 2]

Example 2 concerns an example of the delivery unit which is shown in FIG. 2.

A 10% (w/w) ethanol solution of ethyl cellulose was charged into the interior of a vessel body 2 comprising a body of a capsule which was similar to that of Example 1 and was then discharged therefrom, and the vessel body was dried under vacuum at 60° C. Consequently, a vessel 1 whose interior was covered with a thin film 3 of ethyl cellulose (a water-insoluble substance) having a thickness of about 30 $\mu$m was formed. About 0.15 g of a MS agar medium was charged into this vessel and a somatic embryo of carrot was placed on this medium.

A cap 6 comprising a capsule similar to the above was placed on the vessel 1. At the same time, the positions on the outer surface of the vessel 1 and the inner surface of the cap 6 which were in contact with each other were wetted with water so as to be bonded, a delivery unit having the structure shown in FIG. 2 being thus obtained. All of the operations were conducted under sterile conditions.

The growth conditions of this delivery unit in an incubator at 25° C. were similar to those stated in Example 1. Otherwise, the delivery unit was planted in the soil of a field until the top thereof was buried, whereupon the outer layer of the body and the cap gradually softened or dissolved, and the growth after germination was good.

[EXAMPLE 3]

Example 3 concerns an example of the delivery unit which is shown in FIG. 3.

A cylinder acting as a vessel body having a diameter of 13 mm, a depth of 25 mm, and a thickness of 0.2 mm was formed from ten-one weight ratio mixture of polyvinyl alcohol (trade name PA-05, a partially hydrolized grade having a degree of hydrolysis of 88%, produced by Shin-etsu Chemical Co., Ltd.) and glycerin. A 20% (w/w) metanol solution of polyvinyl acetate was applied to the interior of this vessel body 2, using a thin writing brush, and the vessel was dried with air to form a vessel 1 having the interior covered with a thin film 3 having a thickness of about 20 µm. About 1.5 g of an MS agar medium containing 2 g/l of sucrose was charged into the vessel 1. An adventitious bud of chrysanthemum (Aster sp.) was inserted vertically into this medium so that a length of about 2 mm of the base thereof was embedded in the medium. A film of polyvinyl pyrrolidone (trade name PVP K-30, produced by G. A. F. Co., Ltd.) having a thickness of about 20 µm was wetted with water and bonded to the open end of the vessel 1 so as to form a cap 6. As a result, the delivery unit shown in FIG. 3 was obtained. These operations were conducted under sterile conditions.

When this delivery unit was placed in a field, the cap 6 and the vessel body 2 were dissolved by water contained in the soil and rainwater, and the adventitious bud grew well.

[EXAMPLE 4]

Example 4 concerns another example of the delivery unit shown in FIG. 2.

A small amount of a 10% (w/w) toluene solution of polychloroprene (prepared by diluting a rubber adhesive available on the market) was poured into the interior of a vessel body 2 comprising a body of a capsule which was by turning the vessel body 2 at an angle, then dried at 50° C. under vacuum. As a result, a vessel 1 whose interior was covered with a thin film 3 of chloroprene (a water-insoluble substance) having a thickness of about 50 µm was formed. About 0.15 g of a White agar medium containing 200 mg/l of yeast extract was charged into the vessel 1, and a zygotic embryo produced by a species cross between cabbage and white rape was placed on the medium. A cap 6 which was formed of polyvinyl pyrrolidone (trade name PVP K-15, produced by G. A. F. Co., Ltd.), and which had a form similar to the cap of the Japanese pharmacopoeia No. 1 capsule, was bonded to the body by applying a small amount of an aqueous solution of polyvinyl alcohol PA-05 to the contact positions thereof so as to form a delivery unit similar to that shown in FIG. 2. These operations were conducted under sterile conditions. The behavior of the delivery unit in a field was similar to that described in Example 3.

[EXAMPLE 5]

Example 5 concerns an example of the delivery unit shown in FIG. 5.

A hole having a diameter of 2 mm was formed in the bottom of a vessel body 2 which comprised the body of the Japanese pharmacopoeia No. 00 capsule formed of gelatin (a water-soluble substance) containing glycerin as a plasticizer. And an acrylic white paint available on the market was applied to the interior of the vessel body 2 and the hole 1a, using a thin writing brush, and dried with air to form a vessel 1 whose interior was covered with a thin film 3 having a thickness of about 60 µm. About 0.4 g of an MS agar medium containing 100 ppm of benomyl (trade name Benlate, a fungicide produced by Du Pont Co., Ltd.) was charged into this vessel, and the root axis of a somatic embryo of carrot was inserted into the medium in a state in which the shoot axis thereof was exposed to the air, so that the delivery unit shown in FIG. 5 was obtained.

When the lower half of this delivery unit was embedded in the soil in a field, the vessel body 2 which formed an outer layer was gradually dissolved by water contained in the soil until only the thin film 3 remained after about 10 days. The somatic embory of carrot grew well.

EXAMPLE 6]

Example 6 concerns an example of the delivery unit which is shown in FIG. 7.

A shallow box-shaped vessel body 2 having a length, width, and thickness of about 100 mm, 200 mm, and 20 mm, respectively, was formed from hydroxyethyl cellulose (a water-soluble substance) (trade name Natrosol 250L, produced by Hercules Inc.).

A 10% (w/w) ethanol solution of ethyl cellulose was sprayed to the interior of the vessel body 2 to form a thin film 3 of ethyl cellulose (a water-insoluble substance) having a thickness of about 20 µm so that a vessel 1 was formed. An MS agar medium containing 2 ppm of benzyl aminopurine charged into the vessel to a thickness of about 10 mm. About 1000 adventitious buds of rice (Oryza sativa japonica) were scattered over this medium so that they did not overlap each other, and a cap 6a made of polystyrol, which is a water-insoluble substance, was placed on the vessel so as to form a delivery unit having the structure shown in FIG. 7. These operations were conducted under sterile conditions. The adventitious buds rooted after 7 days in an incubator at 25° C. Then, when the cap 6a was removed and the vessel was placed on outdoor soil, the outer layer which formed the vessel body 2 gradually dissolved until only the ethyl cellulose layer remained. The adventitious buds grew well and good rice seedlings were obtained.

The delivery units of the present invention are described above with reference to examples, but, as a matter of course, the invention is not limited to the above-described examples. Any delivery units which have a fundamental structure similar to that of the examples and which can achieve the same object as the above may be employed.

For example, an adhesive layer may be interposed between the vessel body 2 or the cap body 2a and the thin film 3 or 3a.

In addition, multiple layers of water-insoluble substances which are either homogeneous or heterogeneous may be formed as the thin film 3 or 3a so that it is possible to improve the impermeability thereof.

The delivery units shown respectively in FIGS. 4 and 6 are not described in the examples but, as a matter of course, similar objects to those given in the examples can be achieved by these delivery units.

The present invention described above can provide the effects given below.

Hydrogel is charged into a vessel formed by covering the interior of a vessel body comprising a water-soluble substance with a water-insoluble substance, and a meristematic tissue is brought into contact with the hydrogel in a state in which at least part of the tissue is exposed to the air, so as to form a delivery unit provided with a vessel which has good shape retention. This makes it possible to facilitate the handling of the delivery unit until it is seeded, and to simultaneously supply water and nutrients to the meristematic tissue from the hydrogel and oxygen in the air. Furthermore, when the delivery unit is seeded, the vessel body is dissolved by water from the field and the hindering of germination and rooting of the meristematic tissue can be prevented, whereby a delivery unit having seed functions such as excellent germinating and root-forming abilities can be provided.

What is claimed is:

1. A delivery unit of plant tissue which comprises:
   a vessel having a water-soluble body and an interior covering of a water-insoluble material;
   said vessel being charged with a hydrogel; and
   meristematic tissue which has the ability to grow into an entire plant body through differentiation and which is received in said vessel.

2. A delivery unit of plant tissue according to claim 1 characterized in that said meristematic tissue is held by said hydrogel in a state in which at least part of said meristermtic tissue is exposed to the air.

3. A delivery unit of plant tissue according to claim 1 characterized in that said meristematic tissue is tissue selected from the group consisting of somatic tissue, zygotic tissue, and germ line tissue.

4. A delivery unit of plant tissue according to claim 3 characterized in that said somatic tissue is tissue selected from the group consisting of difinite bud, adventitious bud, somatic embryo, shoot primordium, protocorm-like body, and green spot.

5. A delivery unit of plant tissue according to claim 1 characterized in that said hydrogel is prepared from one of substances selected from the group consisting of agar, sodium alginate, pectine, mannan, carrageenan, and gellan gum.

6. A delivery unit of plant tissue according to claim 1 characterized in that said hydrogel contains nutrient and/or plant growth hormone which promote the growth of said meristermatic tissue.

7. A delivery unit of plant tissue according to claim 1 characterized in that said hydrogel contains one or more substances selected from at least one of the groups of fungicides, bactericides, water-retaining agents, and pH adjusting agents.

8. A delivery unit of plant tissue according to claim 1 characterized in that said water-soluble substance is water-soluble polymeric substance.

9. A delivery unit of plant tissue according to claim 8 characterized in that said water-soluble polymeric substance is substance selected from the group consisting of gelatin, casein, starch, pullulan, sodium alginate, methyl cellulose, hydroxyethyl cellulose, hydroxypropyl cellulose, hydroxypropylmethyl cellulose, polyvinyl alcohol, sodium polyacrylate, polyacrylamide, polyoxyethylene, and polyvinyl pyrrolidone.

10. A delivery unit of plant tissue according to claim 1 characterized in that said water-insoluble substance is substance selected from the group consisting of resin, rubber, cellulose derivative, fat, oil, and wax.

11. A delivery unit of plant tissue according to claim 1 characterized in that said vessel is of a closed type.

12. A delivery unit of plant tissue according to claim 11 characterized in that said vessel comprises a vessel body made of water-soluble substance, thin film of water-insoluble substance applied to the interior of said vessel body, and a cap made of water-soluble substance.

13. A delivery unit of plant tissue according to claim 12 characterized in that the interior of said cap is covered with thin film of water-insoluble substance.

14. A delivery unit of plant tissue according to claim 1 characterized in that said vessel is of an open type.

15. A delivery unit of plant tissue according to claim 14 characterized in that said vessel is made of water-soluble substance and comprises a vessel body open in an upper portion thereof and thin film of water-insoluble substance which is applied to the interior of said vessel body.

16. A delivery unit of plant tissue according to claim 15 characterized in that said vessel body is provided at the open portion thereof with a detachable cap.

17. A delivery unit of plant tissue according to claim 15 characterized in that a hole is formed in at least the bottom of said vessel.

18. A delivery unit of plant tissue according to claim 2 characterized in that said meristematic tissue is held by said hydrogel in a state in which at least the root or a rooting portion thereof is embedded therein.

19. A delivery unit of plant tissue according to claim 1 characterized in that said meristematic tissue is placed on the surface of said hydrogel.

* * * * *